United States Patent
Corman

(10) Patent No.: US 10,278,633 B1
(45) Date of Patent: May 7, 2019

(54) SYSTEMS AND METHODS FOR ASSISTING DIAGNOSING AND/OR TITRATING MEDICATION FOR PREDETERMINED CONDITIONS AND ASSESSING THE EFFECTIVENESS OF MEDICATION PRESCRIBED FOR A PREDETERMINED CONDITION

(71) Applicant: Corman Attention Technologies, LLC, Los Alamitos, CA (US)

(72) Inventor: Clifford L. Corman, Long Beach, CA (US)

(73) Assignee: CORMAN ATTENTION TECHNOLOGIES, LLC, Los Alamitos, CA (US)

( * ) Notice: Subject to any disclaimer, the term of this patent is extended or adjusted under 35 U.S.C. 154(b) by 0 days.

(21) Appl. No.: 14/747,505

(22) Filed: Jun. 23, 2015

Related U.S. Application Data

(60) Provisional application No. 62/016,056, filed on Jun. 23, 2014, provisional application No. 62/025,454, filed on Jul. 16, 2014.

(51) Int. Cl.
*A61B 5/16* (2006.01)
*A61B 5/00* (2006.01)
*G06K 9/62* (2006.01)

(52) U.S. Cl.
CPC .............. *A61B 5/168* (2013.01); *A61B 5/162* (2013.01); *A61B 5/4088* (2013.01); *A61B 5/4848* (2013.01); *G06K 9/6267* (2013.01)

(58) Field of Classification Search
CPC ..... A61B 5/168; A61B 5/4848; A61B 5/4088; A61B 5/162; A61B 5/1118
See application file for complete search history.

(56) References Cited

U.S. PATENT DOCUMENTS 5,377,100 A 12/1994 Pope et al.
5,983,129 A 11/1999 Cowan et al.
(Continued)

FOREIGN PATENT DOCUMENTS

WO 01/54599 A2 8/2001

OTHER PUBLICATIONS

Corman, Clifford L., et al. "The Assessment of Medication Effects in Attention Deficit Disorder Using the Test of Variables of Attention (TOVA)." CyberPsychology & Behavior 3.3 (2000): 509-515.*
(Continued)

*Primary Examiner* — David J. McCrosky
(74) *Attorney, Agent, or Firm* — Rita C. Chipperson; Chipperson Law Group P.C.

(57) ABSTRACT

Systems and methods for assisting with diagnosing and/or titrating medication for predetermined conditions and/or assessing the effectiveness of medication prescribed for a predetermined condition including, but not limited to, Attention Deficit Disorder ("ADD") and Attention Deficit Hyperactivity Disorder ("ADHD"). A diagnostic test is provided that includes display of both target and non-target images. Responses to these display images are analyzed to measure subject criteria including response time consistency, response time, impulsivity, omissions, multiple responses, and guessing. Such data, or numerical quantifiers calculated from such data, may be used to assist with titrating medication for one or more predetermined conditions and/or assessing the effectiveness of medication prescribed for a predetermined condition.

8 Claims, 8 Drawing Sheets

(56) References Cited

U.S. PATENT DOCUMENTS

| | | | |
|---|---|---|---|
| 6,053,739 A | 4/2000 | Stewart et al. | |
| 6,186,145 B1 | 2/2001 | Brown | |
| 6,743,182 B2 | 6/2004 | Miller et al. | |
| 7,452,336 B2* | 11/2008 | Thompson | A61B 5/162 351/203 |
| 7,942,828 B2 | 5/2011 | Teicher et al. | |
| 8,078,253 B2 | 12/2011 | Teicher et al. | |
| 2003/0233032 A1 | 12/2003 | Teicher et al. | |
| 2008/0021351 A1 | 1/2008 | Teicher et al. | |
| 2008/0220400 A1 | 9/2008 | Cox et al. | |
| 2011/0118556 A1 | 5/2011 | Siegel et al. | |
| 2011/0208437 A1 | 8/2011 | Teicher | |
| 2011/0208439 A1 | 8/2011 | Teicher | |
| 2015/0294585 A1* | 10/2015 | Kullok | A61B 5/4088 434/236 |
| 2015/0294587 A1* | 10/2015 | Kullok | A61B 5/4088 434/236 |

OTHER PUBLICATIONS

Lee, J. M., et al. "A study on the system for treatment of ADHD using virtual reality." Engineering in Medicine and Biology Society, 2001. Proceedings of the 23rd Annual International Conference of the IEEE. vol. 4. IEEE, 2001.*

Nydén, Agneta, et al. "Adults with autism spectrum disorders and ADHD neuropsychological aspects." Research in Developmental Disabilities 31.6 (2010): 1659-1668.*

* cited by examiner

Normalized First Quarter Test Values for Female Aged 40-49

| | 1Q | 2Q | 3Q | 4Q | 1H | 2H | Full |
|---|---|---|---|---|---|---|---|
| response mean | 454.16 ms | 467.55 ms | 420.22 ms | 409.76 ms | 461.74 ms | 416.11 ms | 423.73 ms |
| response std dev | 66.41 ms | 74.28 ms | 70.41 ms | 71.45 ms | 69.07 ms | 69.73 ms | 66.82 ms |
| variability mean | 89.22 ms | 69.4 ms | 81.64 ms | 79.96 ms | 73.14 ms | 83.34 ms | 84.94 ms |
| variability std dev | 27.99 ms | 28.73 ms | 28.38 ms | 29.15 ms | 24.87 ms | 25.64 ms | 23.93 ms |
| commission mean | 0.62% | 0.45% | 7.79% | 8.15% | 0.50% | 7.87% | 2.19% |
| commission std dev | 1.25% | 1.18% | 9.02% | 8.85% | 1.08% | 7.89% | 2.24% |
| omission mean | 0.27% | 0.34% | 0.31% | 0.31% | 0.31% | 0.31% | 0.31% |
| omission std dev | 1.01% | 1.30% | 0.68% | 1.30% | 0.92% | 0.99% | 0.90% |

FIG. 6

SYSTEMS AND METHODS FOR ASSISTING DIAGNOSING AND/OR TITRATING MEDICATION FOR PREDETERMINED CONDITIONS AND ASSESSING THE EFFECTIVENESS OF MEDICATION PRESCRIBED FOR A PREDETERMINED CONDITION

CROSS-REFERENCE TO RELATED APPLICATIONS

This application claims the benefit of the U.S. provisional patent applications entitled "Systems and Methods for Assisting Diagnosing and/or Titrating Medication for Pre-determined Conditions", having Ser. No. 62/016,056, filed Jun. 23, 2014, and 62/025,454, filed Jul. 16, 2014, each of which is hereby incorporated by reference in its entirety as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright whatsoever.

BACKGROUND OF THE INVENTION

Embodiments of the present invention generally relate to systems and methods for assisting diagnosing and/or titrating medication for predetermined conditions and assessing the effectiveness of medication. More specifically, the present invention relates to systems and methods for assisting diagnosing and/or titrating medication for predetermined conditions and assessing the effectiveness of medication prescribed for a predetermined condition including, but not limited to, Attention Deficit Disorder ("ADD") and Attention Deficit Hyperactivity Disorder ("ADHD").

BRIEF SUMMARY OF THE INVENTION

Briefly stated, in one aspect of the present invention, a non-transitory computer readable medium for assisting diagnosing or titrating medication for predetermined conditions and assessing the effectiveness of medication prescribed for a predetermined condition is provided. The medium includes instructions stored thereon, which when executed on a processor, perform the steps of: sequentially displaying a plurality of images to a user via an output device for a duration of a first timer, each of the plurality of images displayed upon the expiration of a second timer; recording a display time associated with the display of each of the plurality of images; recording a type of each of the plurality of images; recording inputs inputted by the user; recording an input time associated with the inputs; classifying the inputs; and recording one of the group consisting of performance characteristics, a numerical identifier, and combinations thereof.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 6 is an exemplary table of normalized test values for a female aged 40-49.

DETAILED DESCRIPTION OF THE INVENTION

Figure 1A:
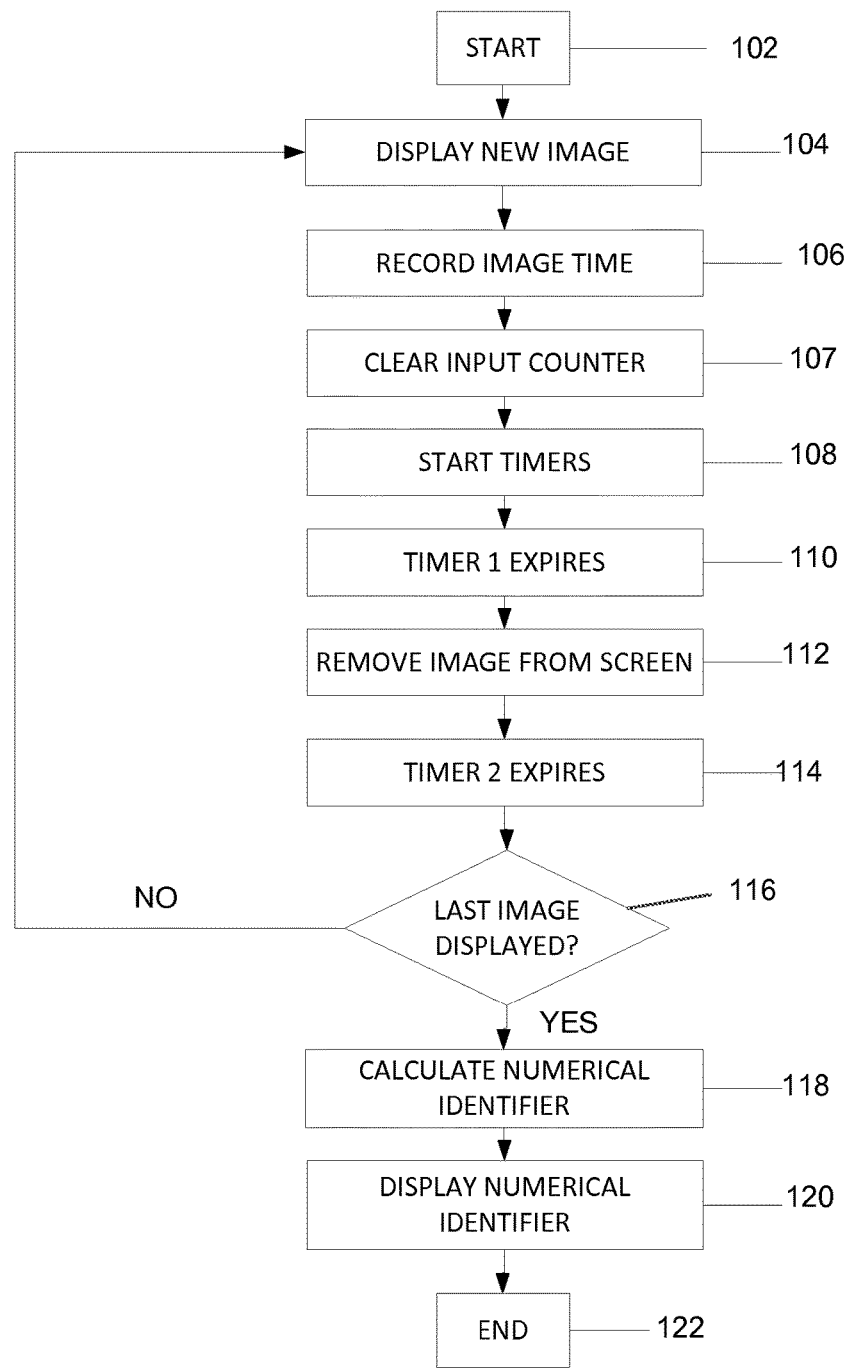
FIG. 1A depicts a flowchart of one method for presenting a stimulus and, optionally, a quantifier to a user in accordance with one embodiment of the present invention.

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import.

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a target" may include a plurality of targets. Thus, for example, a reference to "a method" may include one or more methods and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

The present invention relates to systems and methods for assisting diagnosing and/or titrating medication for predetermined conditions and assessing the effectiveness of medication prescribed for a predetermined condition including, but not limited to, Attention Deficit Disorder ("ADD") and Attention Deficit Hyperactivity Disorder ("ADHD").

In one embodiment of the present invention, the systems and methods for assisting diagnosing and/or titrating medication for a predetermined condition and assessing the effectiveness of medication prescribed for a predetermined condition include administration of a diagnostic test to the subject under diagnosis. In one embodiment of the present invention, the test is in the form of a downloadable application or local target viewer application such as that available for personal computers and/or mobile devices via electronic application stores such as Google Play™, Apple® iTunes®, and the like. However, alternate embodiments of such a test may be substituted including, without limitation, physical tests in which a subject responds to stimulus seen via a monitor via pressing one or more physical buttons or the like.

Figure 2:
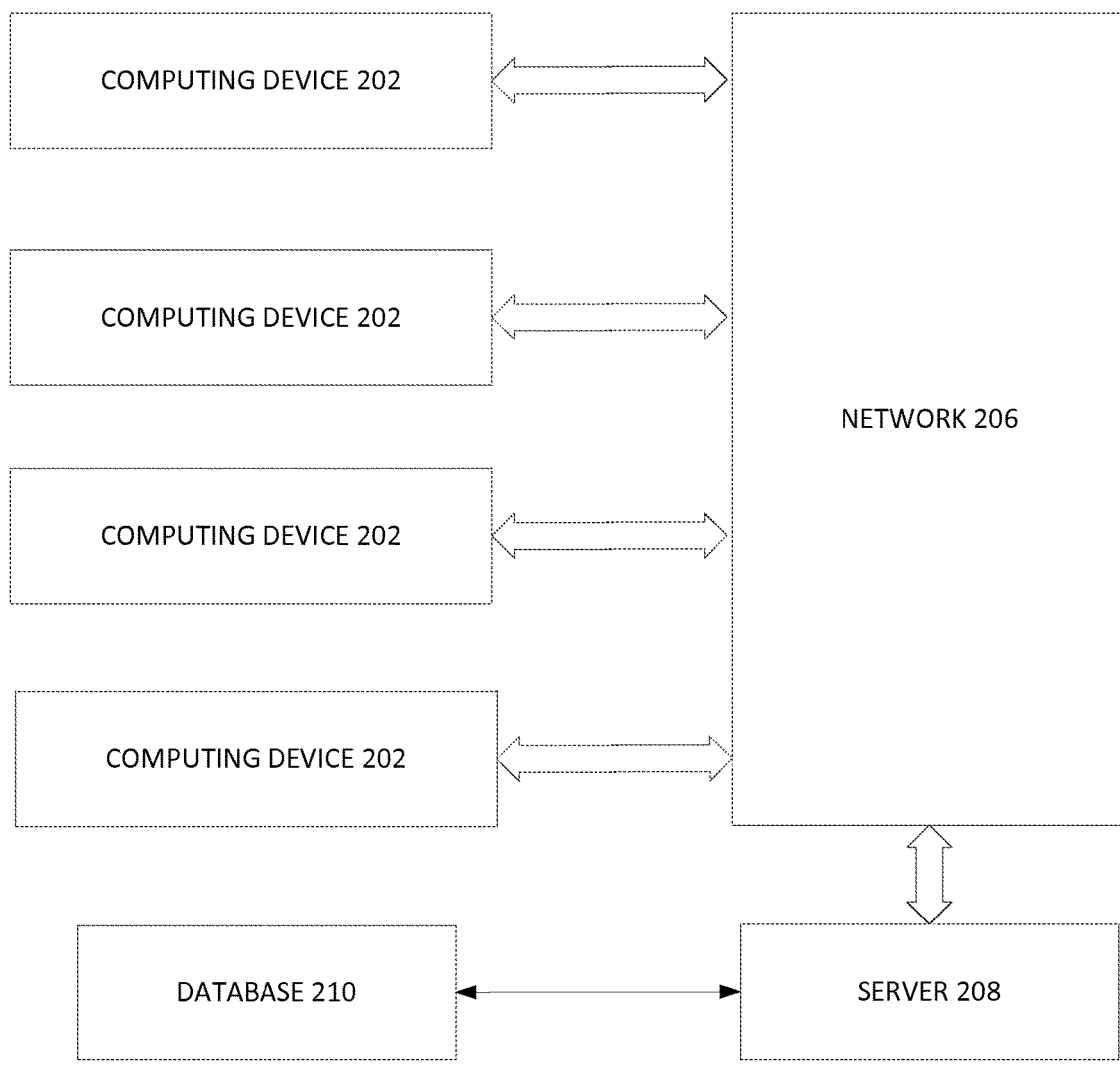
FIG. 2 depicts a schematic view of an exemplary network environment within which various embodiments of the present invention may be implemented.

Referring now to FIG. 2, depicted is an exemplary computing system environment for allowing a user of system 200 to perform the methods described herein. The depicted computing system environment is only one example of a suitable computing environment and is not intended to suggest any limitation as to the scope of use or functionality. Numerous other general purpose or special purpose computing system environments or configurations may be used. Examples of well-known computing systems, environments, and/or configurations that may be suitable for use include, but are not limited to, personal computers ("PCs"), server computers, handheld or laptop devices, multi-processor systems, microprocessor-based systems, network PCs, minicomputers, mainframe computers, cell phones, tablets, embedded systems, distributed computing environments that include any of the above systems or devices, and the like.

Computer-executable instructions such as program modules executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

Figure 3:
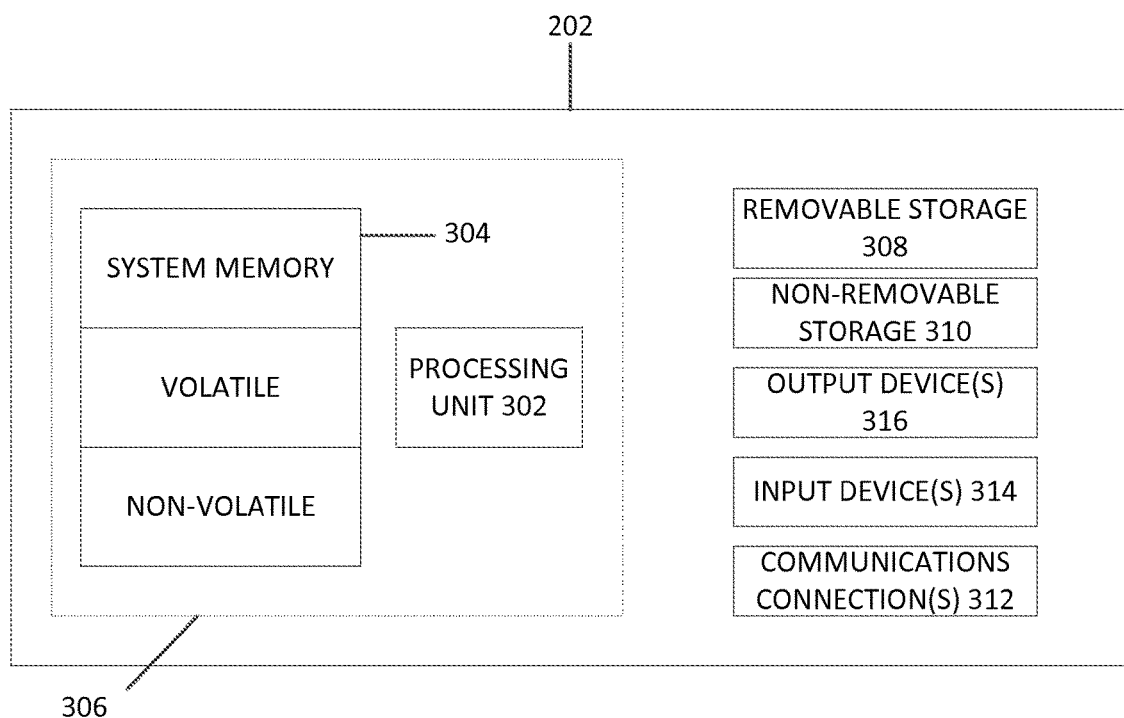
FIG. 3 depicts a block diagram of an exemplary computing device within which various embodiments of the present invention may be implemented.

In the depicted embodiment, exemplary system 200 includes, inter alia, one or more computing devices 202 and server 208, which interface to each other via network 210. In its most basic configuration, as depicted in FIG. 3, computing device 202 includes at least one processing unit 302 and at least one memory 304. Depending on the exact configuration and type of the computing device, memory 304 may be volatile (such as random access memory ("RAM")), non-volatile (such as read-only memory ("ROM"), flash memory, etc.), or some combination of the two. This most basic configuration is illustrated in FIG. 3 by dashed lines 306. In addition to that described herein, computing devices 202 can be any web-enabled handheld device (e.g., cell phone, smart phone, or the like) or personal computer including those operating via Android™, Apple®, and/or Windows® mobile or non-mobile operating systems.

Computing device 202 may have additional features/functionality. For example, computing device 202 may include additional storage (removable and/or non-removable) including, but not limited to, magnetic or optical disks or tape, thumb drives, and external hard drives as applicable. Such additional storage is illustrated in FIG. 3 by removable storage 308 and non-removable storage 310.

Computing device 202 typically includes or is provided with a variety of computer-readable media. Computer-readable media can be any available media that can be accessed by computing device 202 and includes both volatile and non-volatile media, removable and non-removable media. By way of example, and not limitation, computer-readable media may comprise computer storage media and communication media.

Computer storage media includes volatile and non-volatile, removable and non-removable media implemented in any method or technology for storage of information such as computer-readable instructions, data structures, program modules or other data. Memory 304, removable storage 308, and non-removable storage 310 are all examples of computer storage media. Computer storage media includes, but is not limited to, RAM, ROM, electrically erasable programmable read-only memory ("EEPROM"), flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can accessed by computing device 202. Any such computer storage media may be part of computing device 202 as applicable.

Computing device 202 may also contain communications connection(s) 312 which allow the device to communicate with other devices. Such communications connection(s) 312 are an example of communication media. Communication media typically embodies computer-readable instructions, data structures, program modules and/or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency ("RF"), infrared and other wireless media. The term computer-readable media as used herein includes both storage media and communication media.

Computing device 202 may also have input device(s) 314 such as keyboard, mouse, pen, voice input device, touch input device, etc. Output device(s) 316 such as a display, speakers, printer, etc. may also be included. All these devices are generally known to the relevant public and therefore need not be discussed in any detail herein except as provided.

Notably, referring back to FIG. 2, computing device 202 is one of a plurality of computing devices 202 inter-connected by network 206. As may be appreciated, network 206 may be any appropriate network and each computing device 202 may be connected thereto by way of connection 312 in any appropriate manner, and each computing device 202 may communicate with one or more of the other computing devices 202 via network 206 in any appropriate manner. For example, network 206 may be a wired network, wireless network, or a combination thereof within an organization or home or the like, and may include a direct or indirect coupling to an external network such as the Internet or the like. Likewise, network 206 may be such an external network including, without limitation, the Internet.

Computing device 202 may connect to server 208 via such an internal or external network. Although FIG. 2 depicts computing device 202 located in close proximity to server 208, this depiction is not intended to define any geographic boundaries. For example, when network 206 is the Internet, computing device can have any physical location. For example, computing device may be a tablet, cell phone, personal computer, or the like located at any user's office, home, a performance venue for the talent, etc. Or computing device could be located proximate to server 208 without departing from the scope hereof. Also, although FIG. 2 depicts computing devices 202 coupled to server 208 via network 206, computing devices may be coupled to server 208 via any other compatible networks including, without limitation, an intranet, local area network, or the like.

The depicted embodiment of system 200 uses a standard client server technology architecture, which allows users of system 200 to access information stored in relational databases 210 via custom user interfaces. The application is hosted on a server such as server 208 which is accessible via the Internet using a publically addressable Uniform Resource Locator ("URL"). For example, users can access exemplary system 200 using any web-enabled device equipped with a web browser. Communication between software component and sub-systems are achieved by a combination of direct function calls, publish and subscribe mechanisms, stored procedures, and direct SQL queries, however, alternate components, methods, and/or sub-systems may be substituted without departing from the scope hereof.

In some embodiments, system 200 and/or server 208 utilize a PHP scripting language to implement the processes described in detail herein. However, alternate scripting languages may be utilized without departing from the scope hereof.

The exemplary embodiment of the present invention utilizes a Linux variant messaging subsystem. However, alternate messaging subsystems may be substituted including, without limitation, a Windows Communication Foundation ("WCF") messaging subsystem of a Microsoft Windows operating system utilizing a .NET Framework 3.0 programming interface.

Also, in the depicted embodiment, computing device 202 interacts with server 208 via a Transmission Control Protocol/Internet Protocol ("TCP/IP") communications protocol; however, other communication protocols may be substituted.

Computing devices 202 are equipped with one or more Web browsers to allow them to interact with server 208 via a HyperText Transfer Protocol ("HTTP"). HTTP functions as a request-response protocol in client-server computing. For example, a web browser operating on computing device 202 may execute a client application that allows it to interact with applications executed by server 208. The client application submits HTTP request messages to the server. Server 208, which provides resources such as HTML files and other content, or performs other functions on behalf of the client application, returns a response message to the client application upon request. The response typically contains completion status information about the request as well as the requested content. However, alternate methods of computing device/server communications may be substituted without departing from the scope hereof.

In the exemplary system 200, database 210 may include a plurality of database tables. As may be appreciated, database 210 may be any appropriate database capable of storing data and may be included within or connected to server 208 or any plurality of servers similar to 208 in any appropriate manner without departing from the scope hereof.

In the exemplary embodiment of the present invention depicted in FIG. 2, database 210 is a structured query language ("SQL") database(s) with a relational database management system, namely, MySQL as is commonly known and used in the art. Database 210 is resident within server 208. However, other databases may be substituted without departing from the scope of the present invention including, but not limited to, PostgreSQL, Microsoft® SQL Server 2008 MySQL, Microsoft® Access®, and Oracle databases, and such databases may be internal or external to server 208.

It should be understood that the various techniques described herein may be implemented in connection with hardware or software or, as appropriate, with a combination of both. Thus, the methods and apparatus of the presently disclosed subject matter, or certain aspects or portions thereof, may take the form of program code (i.e., instructions, scripts, and the like) embodied in tangible media, such as floppy diskettes, CD-ROMs, hard drives, flash drives, DVDs or any other machine-readable storage medium wherein, when the program code is loaded into and executed by a machine, such as a computer, the machine becomes an apparatus for practicing the presently disclosed subject matter.

In the case of program code execution on programmable computers, the interface unit generally includes a processor, a storage medium readable by the processor (including volatile and non-volatile memory and/or storage elements), at least one input device, and at least one output device. One or more programs may implement or utilize the processes described in connection with the presently disclosed subject matter (e.g., through the use of an application-program interface ("API"), reusable controls, or the like). Such programs may be implemented in a high-level procedural or object-oriented programming language to communicate with a computer system. However, the program(s) can be implemented in assembly or machine language, if desired. In any case, the language may be a compiled or interpreted language, and combined with hardware implementations.

Although exemplary embodiments may refer to utilizing aspects of the presently disclosed subject matter in the context of one or more stand-alone computer systems, the subject matter is not so limited, but rather may be implemented in connection with any computing environment, such as system 200 or a distributed computing environment. Still further, aspects of the presently disclosed subject matter may be implemented in or across a plurality of processing chips or devices, and storage may similarly be affected across a plurality of devices in system 200. Such devices might include personal computers, network servers, and handheld devices (e.g., cell phones, tablets, smartphones, etc.), for example.

In the exemplary embodiment, server 208 and its associated databases are programmed to execute a plurality of processes including those discussed in greater detail below. Some such processes include process 100 that presents a diagnostic test to the subject being diagnosed as discussed herein with respect to FIG. 1A and process 1100 that processes an input from a test taker as discussed herein with respect to FIG. 1B.

In the embodiment described herein, there are two versions of the diagnostic test. One version is intended for non-professional use (e.g., for use by a parent for a child) and a second version is intended for professional use (e.g., for use by physicians and the like responsible for diagnosing the predetermined condition associated with the diagnostic tests). More specifically, in one embodiment of the present invention, the non-professional version of the test may gather data and provide statistical analysis to non-professionals, who may use this information to determine whether the subject should seek professional advice and diagnosis, wherein such diagnosis may include the prescription of medication. Also, in one embodiment of the present invention, the professional version of the test may gather data that may be used by the professional to assist with making a diagnosis and/or titrating medication. Both versions of the test may be utilized to assisting with diagnosing and/or titrating medication and/or to assess the effectiveness of a medication prescribed for a predetermined condition via re-administration of the test to the subject after the medication has been taken by the subject and a sufficient time has passed to allow the medication to have the necessary impact on the subject.

In one embodiment of the present invention, a process such as process 100 provides target images and non-target images to the subject being diagnosed via the subject's computing device 202. For example, if the subject is performing the test on a cell phone type computing device 202, the target will appear on an output device 316 thereof (e.g., the cell phone screen).

Figure 4A:
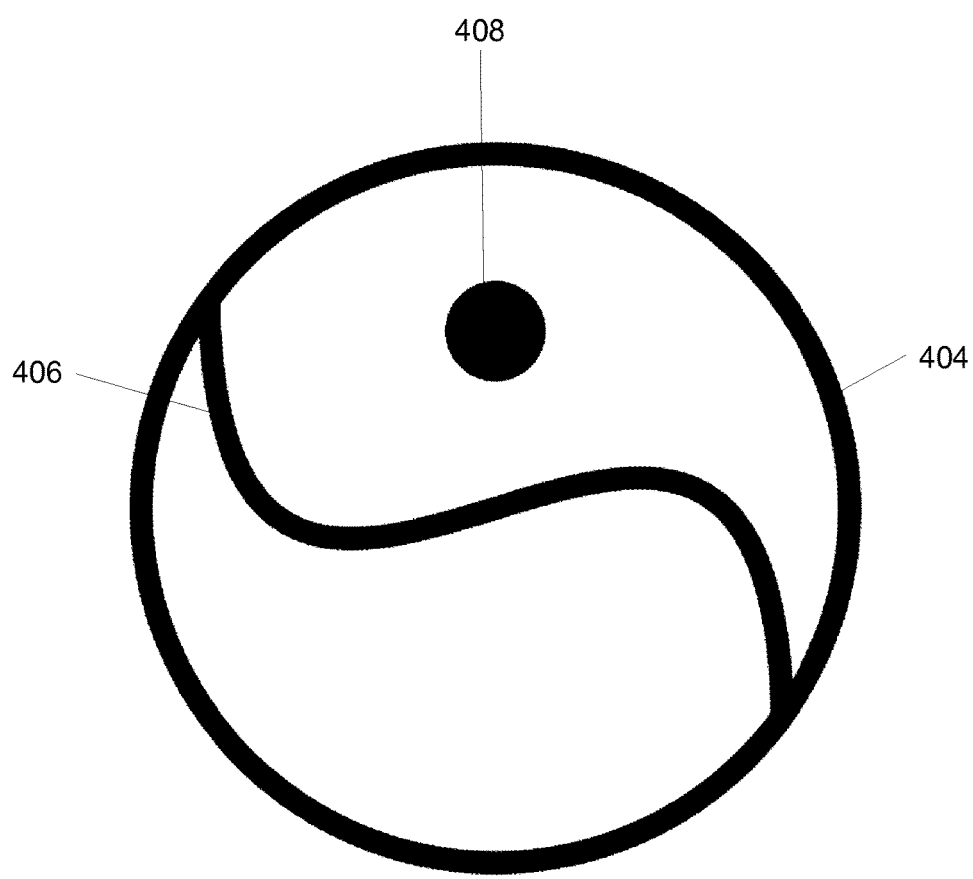
FIGS. 4A and 4B are a target and non-target, respectively, for use in administering a diagnostic test in accordance with one embodiment of the present invention.
Figure 4B:
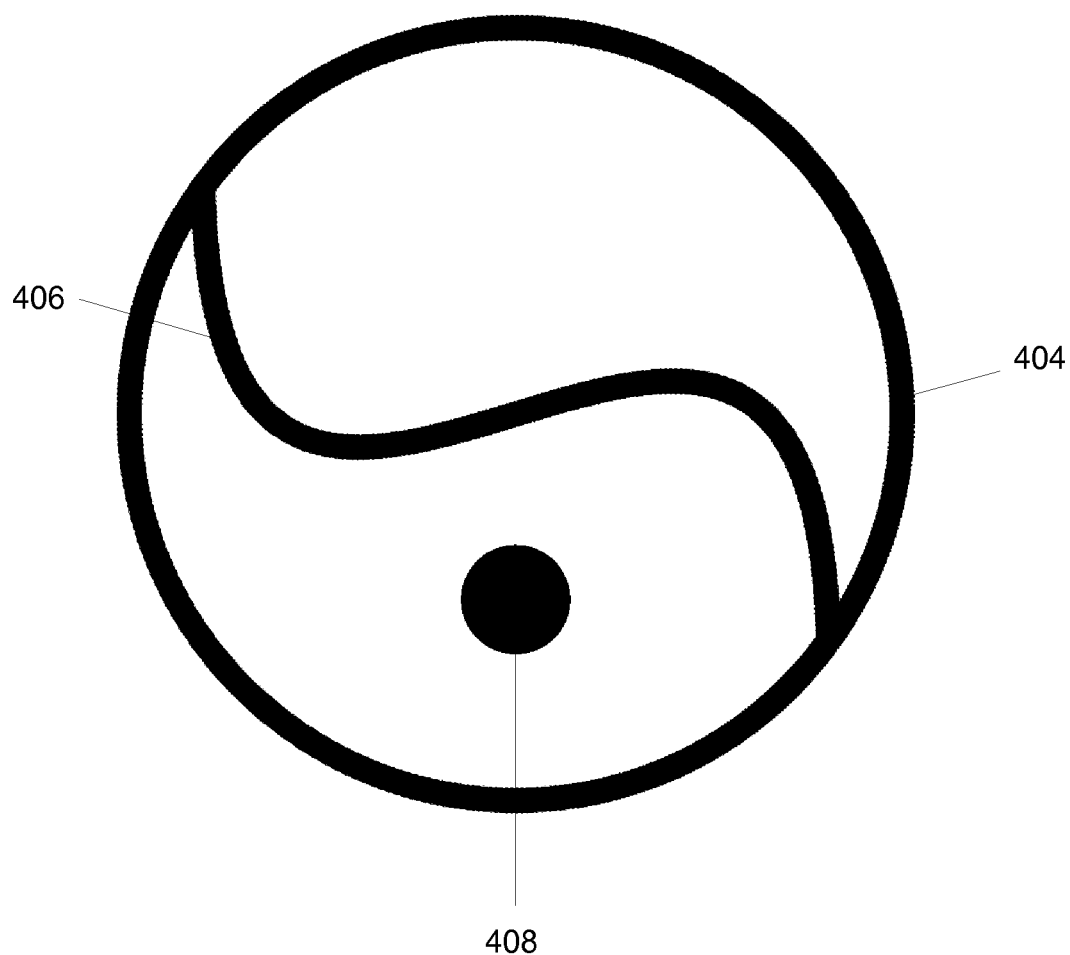

In one embodiment of the present invention, target 400 and non-target 402 are as shown in FIGS. 4A and 4B, respectively. Process 100 will sequentially flash an image of target 400 or non-target 402 as described in greater detail herein. Both target 400 and non-target 402 include a substantially circular perimeter 404, a reverse S-shaped divider 406, and a substantially solid dot 408. However, in target 400, dot 408 is located above divider 406, and in non-target 402, dot 408 is located below divider 406. That is, the target is a substantially inverse pattern relative to the non-target. However, alternate images may be substituted for the target and non-target including, without limitation, images that do not have an inverse pattern.

In the depicted embodiment, the ratio of the diameter of substantially circular perimeter 404 to the diameter of dot 408 is approximately seven (7) to one (1). However, alternate targets and/or non-targets including, but not limited to, those with varying ratios and designs may be substituted without departing from the scope of the present invention.

In one embodiment of the present invention, either target 400 or non-target 402 is flashed every two seconds. The subject taking the test is directed to push a button (either physical or depicted via a touch screen) via a computing device such as computing device 202 whenever target 400 is flashed. The subject is directed to not press the button, not tap the screen, or the like when non-target 402 is flashed. The responses are then measured in milliseconds and recorded via the application in a database such as database 210 in communication with a server such as server 208 and the subject's computing device. The responses are also analyzed to determine one or more test taking performance characteristics of the test taker including, without limitation, response time consistency (RTC), response time (RT), impulsivity (I), omissions (O), multiple responses (MR), and guessing (G). Optionally, a numerical quantifier may also be calculated during such analysis and such numerical quantifier may be utilized to assist with diagnosing and/or titrating medication to treat a predetermined condition and/or to assess the effectiveness of medication prescribed for a predetermined condition. Or, if a numerical quantifier is not calculated, the results of the diagnostic test may optionally be otherwise utilized for the purpose of assisting with diagnosing and/or titrating medication for one or more predetermined conditions and/or assessing the effectiveness of medication prescribed for a predetermined condition. The numerical quantifier and/or one or more of the characteristics of the test taker may be functionally displayed to the test taker.

It should be noted that although the above described embodiment requires a response upon the occurrence/appearance of a visual stimulus such as a target, alternate embodiments are envisioned in which the subject responds to an auditory stimulus in lieu of a visual stimulus. For example, in one such embodiment, the subject is directed to respond (e.g., pushing a button, tapping a screen, or the like) when he or she hears a first tone (e.g., an "A" tone in the range above the middle "E" tone) and to not respond when he or she hears a second tone (e.g., a "B" tone in the range below the middle "E" tone).

More specifically, in one embodiment of the present invention, the duration of each test is approximately 21 minutes and 36 seconds and the duration of a half-duration test is approximately 10 minutes and 18 seconds. The half-duration test may be utilized, for example, for testing a small child. Also, each full duration test includes approximately six hundred forty eight (648) events, and a half-duration test includes approximately three hundred and twenty four (324) events, each of such events being the flashing of either the image of a target or non-target stimulus. Each stimulus image is presented for one tenth ($\frac{1}{10}$) of a second and the images are flashed in two (2) second intervals. Each full-duration test includes four (4) quarters, and the half-duration test includes the first and third quarters of a full-duration test. The stimuli images presented in each quarter are presented according to a pattern generated randomly before the test begins. These patterns determine which stimuli images should be presented as targets and non-targets.

The patterns associated with the first two (2) quarters flash stimuli images with a ratio of two (2) targets for every seven (7) non-targets. The patterns associated with the remaining two (2) quarters flash stimuli images with a ratio of seven (7) targets for every two (2) non-targets. However, alternate testing durations, stimulus image quantities, stimulus image show durations, target versus non-target ratios, and pattern quantities may be substituted without departing from the scope hereof. For example, embodiments of the invention are envisioned in which the patterns for all quarters or other subsections of a test flash stimuli images with a ratio of three and one half (3½) targets for each non-target. Alternate embodiments are also envisioned in which different stimuli images are flashed during different portions of the test.

In the depicted embodiment, a quantity of one (1) to nine (9) consecutive target images may appear before a non-target image appears and vice versa. However, other maximum quantities of consecutive target images and/or non-target images may be substituted without departing from the scope hereof.

Since the quantity of stimuli image patterns is effectively unlimited, they provide enough variation that responses are not likely to be predicted even after an individual subject has taken the test multiple times. Furthermore, the mathematical characteristics of the patterns are such that meaningful statistical analysis may be performed with the responses received for multiple subjects and/or multiple testing sessions.

The test is administered according to the pattern representing the selected pattern number. The response status is polled by the application. Each time the subject responds, the application stores the response time in milliseconds relative to the start time of the test. In one embodiment of the present invention, the recorded response times are accurate within plus or minus eight (8) milliseconds. In an alternate embodiment of the present invention in which a physical button is utilized, the recorded response times are accurate within plus or minus one (1) millisecond. This button may be, for example, a micro-switch type input device 314 capable of connecting to a computing device such as computing device 202, both as described in greater detail above.

After testing, system 200 provides testing data and/or a numerical quantifier for all subjects, individual subjects, parents, physicians, and the like via a browser interface. It also allows the user to assign stored test data to a subject and to perform statistical analysis of the stored test data based upon a set of pre-established norms. System 200 also generates and displays to the user various reports on test data and subjects (e.g., quantity and timing of missed and incorrect responses, scores for each quarter of the test, scores for each half of the test, and scores for the full test). System 200 also generates and displays table and graph views of the test variables and scores for a series of tests taken by an individual subject. These tables, which may be arranged by relative medication dosage, assist the user to identify the most effective medication and dosage for a particular subject.

Optionally, system 200 calculates a numerical quantifier for a specific predetermined condition that facilitates the following: 1) aiding professionals in evaluating the results of the test and making a diagnosis; 2) analyzing the test data for a user or subject by calculating reaction time, reaction consistency, incorrect responses, and missed responses; 3) performing statistical analysis in which the calculated variables are compared to population norms for such variables based upon gender and age; and 4) combining the plurality of variables into an aggregate score for the respective predetermined condition.

Referring now to FIG. 1A, depicted is one exemplary process 100 for presenting a stimulus image and, optionally, a numerical quantifier to the test taker. Exemplary process 100 begins at step 102, at which a test taker initiates a test. Such initiation may include double clicking an icon via a mouse, finger, or the like on a display device of a computing device 202. In the exemplary embodiment discussed herein, initiation of the test includes clearing the output device such that a "blank screen" is displayed to the test taker. The blank screen enhances the ability of the test taker to focus on, and respond to, the images to be displayed to the test taker. However, alternate embodiments are envisioned in which the screen includes material and/or images other than the stimulus images described in greater detail herein.

Once a test has been initiated, process 100 proceeds to 104, at which a stimulus or non-stimulus image is displayed to the test taker. Such an image may be as shown in FIG. 4A, which depicts a target stimulus image, and FIG. 4B, which depicts a non-target stimulus image as discussed in greater detail herein.

Next, at step 106, the time at which the image is displayed is recorded. This time is recorded to allow process 100 to calculate various test taking performance characteristics as described in greater detail herein. For example, this time allows process 100 to calculate the response time, i.e., the time that elapses between display of the image and receipt of an input from the test taker (e.g., a screen tap, a mouse click, or the like).

Process 100 then proceeds to step 107, at which an input counter, if utilized, is cleared. An input counter may be utilized to record the quantity of taps input by a test taker in response to a specific image. In such embodiments, when a new image is displayed, the number of taps associated with the previously displayed image (i.e., the number associated with the tap counter before it is cleared) is stored in a database such as database 210 in conjunction with the previously displayed image. The tap counter is then cleared, or set to equal zero taps, for the new image. The tap counter will remain at zero unless/until a user input is received such as, for example at step 1102 of exemplary process 1100 as described in greater detail below.

Process 100 then proceeds to 108, at which a pair of timers, Timer 1 and Timer 2, is started. Timer 1 is the duration of time for which the image will be displayed to the test taker, and Timer 2 is the duration of time between the initial display of consecutive images. In the embodiment of the invention described in FIG. 1A, Timer 1 is set for 0.1 seconds and Timer 2 is set for 2 seconds. That is, the image is displayed to the user on an output device of computing device 202 or the like for a duration of 0.1 seconds, after which Timer 1 expires at 110 and process 100 proceeds to step 112, at which the image is no longer displayed such that the user is again viewing a blank screen. Then, two seconds after the last image was displayed to the user, Timer 2 expires at 114.

Process 100 then proceeds to 116, at which it determines whether the image previously displayed to the test taker was the last image of the test or test portion (e.g., a quarter of the test, a third of the test, a half of the test, etc.). If it was not the last image, process 100 returns to step 104, at which a new target or non-target image is displayed to the user and steps 106 through 116 are repeated until the last image of the test or test portion is displayed. When the last image has been displayed, process 100 proceeds to step 118.

At step 118, a numerical identifier ("NI") is calculated. In the depicted embodiment, the exemplary formula for calculating a NI is as follows:

$$NI=(RTMSD*3)+(RTVMSD*3)+(CMSD*3),$$

wherein RTMSD is the standard deviation of the test taker's Response Time Mean ("RTM") as compared to the normalized RTM test values for a subject of the same sex and age group, RTVMSD is the standard deviation of the test taker's Response Time Variability Mean ("RTVM") as compared to the normalized RTVM test values for a subject of the same sex and age group, and CMSD is the standard deviation of the test taker's Commission Mean ("CM") as compared to the normalized CM test values for a subject of the same sex and age group.

RTM is the average of all response times, wherein the response time is the time that elapses between the display of the stimulus image at, for example, step 104 of process 100 and the time the response is recorded at, for example, step 1104 of process 1100. In the depicted embodiment, the response time is measured in milliseconds; however, alternate time criteria may be substituted without departing from the scope of the present invention. Also, in the depicted embodiment, if the test taker fails to respond to a stimulus, it is disregarded for the purposes of calculating the various test results discussed in greater detail herein. However, alternate embodiments are envisioned in which failure to respond to a displayed image is positively recorded and factored in to the calculation of the test results and/or NI as discussed in greater detail herein.

RTVM is the average variability of response times for an individual subject within a single test. In the depicted embodiment of the present invention, RTVM is calculated by subtracting each individual response time from the response mean. Each of these differences is then squared, and all of the squares are summed. Thereafter, the square root of the sum is calculated, and the result thereof is divided by the number of responses to determine the value of RTVM. However, alternate embodiments of the invention are envisioned in which RTVM is calculated differently.

CM is the average of the percentage of incorrect inputs. In the depicted embodiment, CM is calculated by summing the quantity of incorrect inputs, and then dividing this sum by the quantity of correct inputs, wherein the quantity of the correct inputs is the number of correct inputs if the test were taken perfectly. The resulting value is then multiplied by 100. Also, in the depicted embodiment, incorrect inputs include inputs entered in response to non-target stimulus images as well as any inputs to a target stimulus image after the first input to the image has been recorded. For the latter, for example, if a user enters three inputs to a single stimulus image, the first input is considered a correct input and the second and third inputs are considered incorrect inputs. However, alternate embodiments of the present invention are envisioned in which alternate methods of calculating CM and/or determining an incorrect input are substituted.

It should be noted that this is just one exemplary method of calculating a NI and other methods may be substituted without departing from the scope hereof. Also, calculation of an NI is optional. One or more of the test taking performance characteristics described herein may be utilized without calculation of the NI for the purposes set forth herein.

Next, at step 120, the NI calculated at step 118 is displayed to the user via, for example, an output device of a computing device such as computing device 202. Or, alternatively, one or more of the test taking performance characteristics may be displayed to the user as part of step 120. Or, in yet another alternate embodiment, nothing is displayed to the user but the test taking performance characteristics and/or NI are saved and/or are otherwise provided to a third party to allow such third party to, for example, assist with the titration of medication for a predetermined condition and/or to assess the effectiveness of the test taker's current medication and/or dosage thereof. Thereafter, process 100 proceeds to 122, at which it ends.

Figure 5:
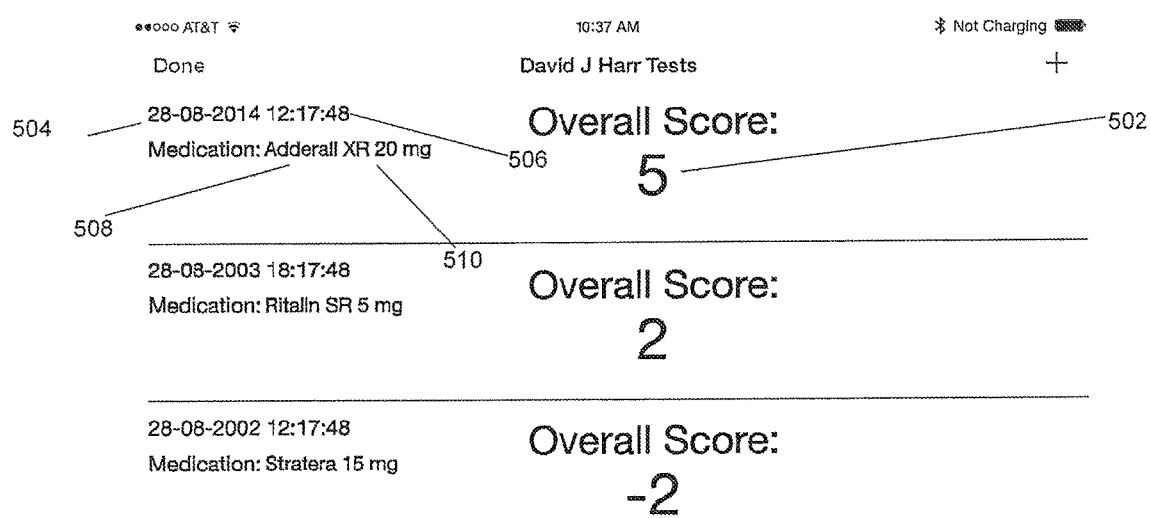
FIG. 5 is an exemplary display of the history of the tests taken by a subject in accordance with one embodiment of the present invention.

Referring now to FIG. 5, depicted is an exemplary display of a NI to a test taker. In the depicted embodiment, then NI 502 is displayed to the test taker along with other information regarding the test including, without limitation, date of test 504, time of test 506, and medication type 508 and dose 510 taken by the test taker prior to taking the test. However, alternate embodiments are envisioned in which, for example, the NI alone is displayed to the user.

In some embodiments of the present invention, the NI indicates to the test taker whether his or her responses are considered within the norm or whether professional treatment and/or diagnosis should be sought. In the depicted embodiment, a score less than zero will be presented to the user in red and indicates the need to seek professional treatment and/or diagnosis. Conversely, a score of zero or higher will be presented in green and indicates that the test taker falls within the norm and further professional treatment and/or diagnosis is not required. However, alternate collars and scales may be substituted without departing from the scope hereof.

Figure 1B:
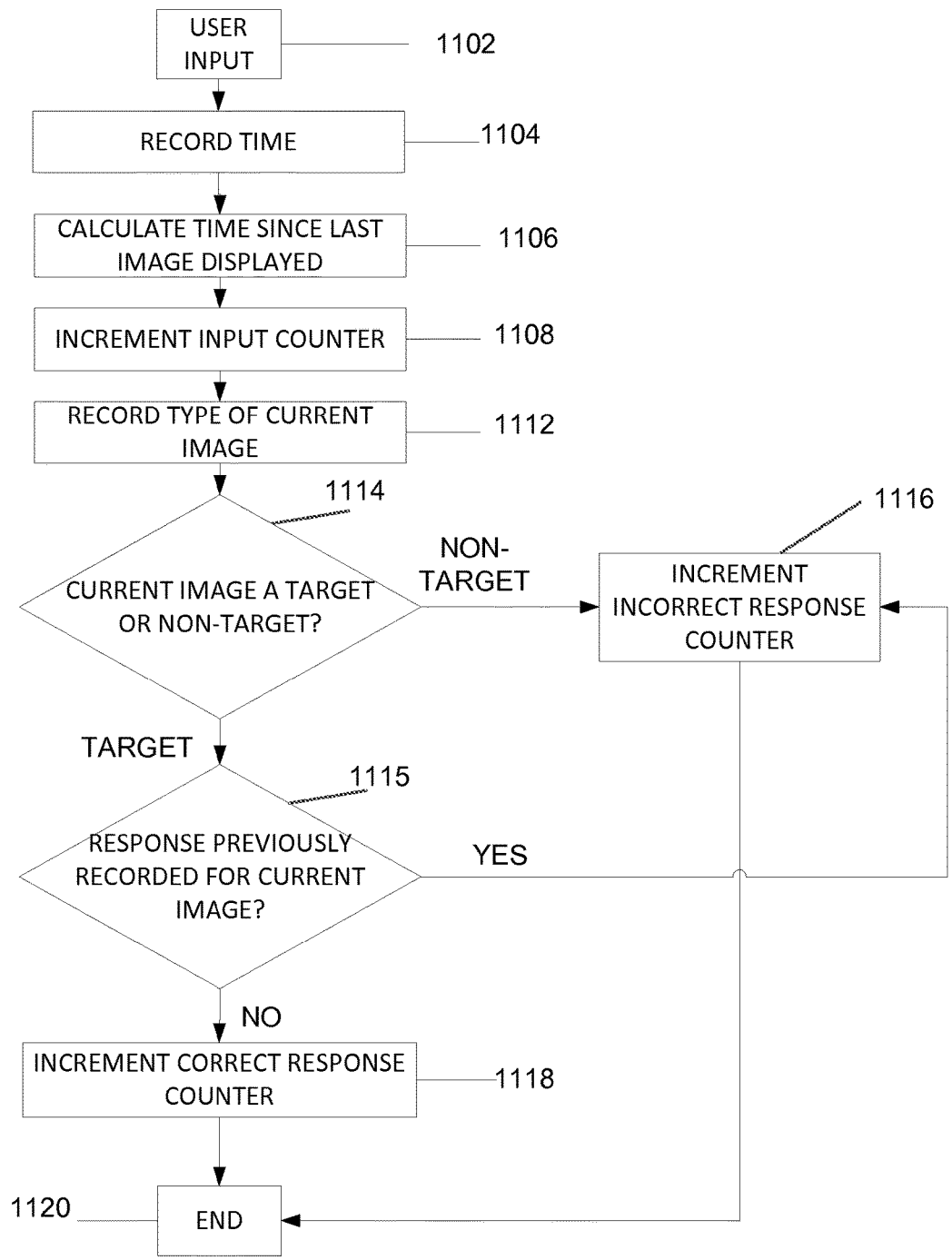
FIG. 1B depicts a flowchart of one method for recording user response to a stimulus in accordance with one embodiment of the present invention.

Turning next to FIG. 1B, depicted is an exemplary process 1100 of one method for recording user response to a stimulus in accordance with one embodiment of the present invention. Process 1100 begins at 1102, at which an input is received from the user/test taker. In the depicted embodiment, such an input is the tapping of the user's finger on the screen of a computing device; however, alternate methods of inputs may be substituted as discussed in greater detail herein.

Next, at 1104, the time at which the input is received is recorded. This time may be recorded in a database such as database 210 as discussed herein with respect to FIG. 2. Process 1100 then proceeds to 1106, at which it calculates the time between receipt of the user's input and display of the last displayed image. The result of this calculation may be stored in a database such as database 210 in connection with the user input and/or the corresponding stimulus image.

Process 1100 then proceeds to 1108, at which the tap counter is incremented. For example, if no user inputs have been received since the display of the last displayed image, the tap counter is incremented from zero to one. Or, if one or more taps had been previously recorded for the last displayed image, the tap counter is incremented by one to indicate the total quantity of user inputs received since the last image was first displayed.

Process 1100 then proceeds to 1112, at which the type of the last displayed image is recorded. In the depicted embodiment, the type of image may be a target image or non-target image. A target image is one for which the test taker is expected to provide an input, and a non-target image is one for which the test taker is not expected to respond. The type of image may be recorded in a database such as database 210 as described with regards to FIG. 2. Next, at 1114, if the last displayed image was a non-target image, process 1100 proceeds to step 1116, at which the incorrect response counter is incremented by one.

Conversely, if at 1114, the last displayed image was a target image, process 1100 proceeds step 1115, at which it is determined whether a response was previously recorded for the current image. If no, process 1100 proceeds to step 1118, at which the correct response counter is incremented by one. If a response was previously recorded for the current image at 1115, process 1100 proceeds to 1116, at which the incorrect response counter is incremented by one since the test-taker/user is directed at the start of the test to respond to a target image only once. The values of the correct and incorrect response counters may be saved, for example, in a database such as database 210. After steps 1116 or 1118, process 1100 proceeds to 1120 at which it ends.

Referring now to FIG. 6, depicted is an exemplary table of normalized values for use in calculating a NI.

In the illustrated embodiment, normalized values such as, for example, normalized RTM test values, normalized RTVM test values, and normalized CM test values are determined based upon age and sex and tables are created for each of the categories.

For example, age categories may be based upon actual year of age for test takers aged four through nineteen. For older test takers, the normalized values are grouped in decades (e.g., 20-29, 30-39, 40-49, 50-59, 60-69, 70-79, and 80+). Also, embodiments of the invention are envisioned in which multiple tables are created for each portion of the test taken. For example, in one such embodiment, seven tables are created to represent the normalized values for the respective age group for the first, second, third, and fourth quarters of the test, the first and second halves of the test, and the test as a whole. In the depicted embodiment, the scores for the whole test are utilized for calculation of the numerical identifier and the values associated with the varying portions of the test are utilized as test taking performance characteristics and/or for other evaluation purposes. However, alternate embodiments of the present invention are envisioned in which the values associated with the varying portions of the test are utilized in the calculation of the numerical identifier.

Additionally, in some embodiments of the present invention, younger children (e.g., ages 4-6) are provided a test of lesser duration than that provided to older children/adults. In such scenarios, tables for each quarter of the test and each half of the test may or may not be populated.

In the table depicted in FIG. 6, normalized first quarter test taking performance characteristics or values are illustrated for females aged 40 to 49. This exemplary table illustrates the following performance characteristics or values: response time mean (RTM), response time mean standard deviation (RTMSD), response time variability mean (RTVM), response time variability mean standard deviation (RTVMSD), commission mean (CM), commission mean standard deviation (CMSD), omission mean (OM), and omission standard deviation (OMSD). All of the values other than OM and OMSD are described in greater detail above. OM is the average percentage of failed responses to a target stimulus image, and OMSD is the standard deviation of the test taker's OM as compared to the normalized OM test values for a subject of the same sex and age group. In the depicted embodiment, OM is calculated by dividing the quantity of IP of target stimulus images to which the subject makes no response by the total quantity of correct responses, wherein the total quantity of correct responses is the quantity that would be entered if the test were taken perfectly. However, tables having alternate performance characteristics and/or values are envisioned without departing from the scope of the present invention. It should be noted that, in the depicted embodiment, the OM value is displayed to the test taker and/or otherwise recorded, however, it is not utilized in calculation of the NI. However, alternate embodiments are envisioned in which the OM value is utilized to calculate the NI or other values without departing from the scope hereof.

In the depicted embodiment, exemplary tables of normalized values are typically utilized to calculate an NI or other results for an un-medicated test taker who is taking an initial, baseline test. Once the test taker's baseline test is recorded, scores for future tests taken by the same test taker will typically be calculated against the test taker's baseline test. In such a scenario, the tables are utilized to provide values for one standard deviation from each metric and those values are used to assign a number to each value in the test (e.g., response time, variability, and commission) by marking their deviation from their own norm in thirds of a standard deviation.

Although one exemplary method of calculating a NI is illustrated, alternate methods may be substituted without departing from the scope hereof.

In some embodiments of the present invention, a practice test is administered prior to administration of the true test in order to familiarize the subject with the form of the test. The subject can cancel this practice test at any time, after which the application provides visual feedback that the true test is about to begin.

Also, in some embodiments of the present invention, the subject is shown a plurality of flashing targets (e.g., ten) to obtain an individualized timing threshold for each test administration. This helps to ensure that the subject is not guessing during the actual test. In such an embodiment, the length of time for which the image is displayed to the test taker may be modified according to the results of the timing threshold test.

In one embodiment of the present invention, the testing application includes various testing options that allow the administrator of the test to choose a test based upon duration of the test, stimulus image patterns to be presented to the subject, and the like.

In some embodiments of the present invention, the subject's identification is kept anonymous via use of a test identification ("ID") number to allow the testing results to be anonymously matched to a subject.

Although the embodiment of the present invention depicted herein is designed to diagnosis or titrate medication for a predetermined condition and/or to assess the effectiveness of medication prescribed for a predetermined condition, the present invention may be used to detect the use of illegal drugs, alcohol, or other response altering substances. For example, the test may be administered to a person during a time at which he or she is not under the influence of such a substance. Thereafter, the test may be re-administered and the resulting score or numerical identifier, as compared to the original score or numerical identifier, may indicate the use of illegal drugs, alcohol, or other response altering substances.

Although several processes have been disclosed herein as software, it may be appreciated by one of skill in the art that the same processes, functions, etc. may be performed via hardware or a combination of hardware and software. Similarly, although the present invention has been depicted as a hardwired system, these concepts may be applied to wireless systems and hybrid hardwired and wireless systems without departing from the scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for assisting diagnosing or titrating medication for predetermined conditions and assessing the effectiveness of medication prescribed for a predetermined condition, to a remote user over a network based upon information received from an individual computing device via the network, said method comprising the steps of:

providing a local target viewer application to the remote user for installation on a first computing device of the remote user, the local target viewer application sequentially displaying a plurality of images to the remote user via an output device for a duration of a first timer, each of said plurality of images displayed upon the expiration of a second timer;

receiving and recording a display time associated with the display of said each of said plurality of images at a server, the display time sent from the first computing device to the server via the network;

receiving and recording a type of said each of said plurality of images at the server, the type sent from the first computing device to the server via the network, each of said plurality of images is selected from the group consisting of a target image and a non-target image, the target image having a substantially inverse pattern relative to the non-target image;

receiving and recording inputs inputted by said remote user at the server, the inputs sent from the first computing device to the server via the network;

receiving and recording an input time associated with said inputs at the server, the input time sent from the first computing device to the server via the network; the server including a memory or database the server storing the remote user's data in said memory or said database, said data including display time, said type of each of said plurality of images, said inputs inputted by said remote user, and said input time associated with said inputs, wherein the server performs the steps of:

calculating a numerical identifier based upon said data;
recording one of the group consisting of performance characteristics, a numerical identifier, and combinations thereof; and
transmitting one of the group consisting of performance characteristics, a numerical identifier, and combinations thereof to the first computing device.

2. A medium according to claim 1, wherein said numerical identifier is calculated by summing three times a standard deviation of a response time mean and three times a standard deviation of a response time variability mean and three times a standard deviation of a commission mean.

3. A medium according to claim 1, wherein if said numerical identifier is less than zero, said remote user is prompted to seek professional treatment.

4. A medium according to claim 1 wherein the server further performs the step of:
displaying said one of the group consisting of said performance characteristics, said numerical identifier, and combinations thereof to said user.

5. A medium according to claim 1, wherein the ratio of display of said target image to said non target image is two to seven during a first half of a test and a ratio of display of said target image to said non target image is seven to two during a second half of a test.

6. A medium according to claim 1 wherein the target image is one for which the test taker is expected to provide an input, and a non-target image is one for which the test taker is not expected to provide an input.

7. A medium according to claim 1,
wherein the target image has a substantially circular perimeter, a reverse S-shaped divider, and a substantially solid dot located above the divider; and
wherein the target image has a substantially circular perimeter, a reverse S-shaped divider, and a substantially solid dot located below the divider.

8. A medium according to claim 7, wherein a ratio of a first diameter of the substantially circular perimeter to a second diameter of the dot is approximately seven to one.

\* \* \* \* \*